United States Patent [19]

Calvo et al.

[11] Patent Number: 4,749,707

[45] Date of Patent: Jun. 7, 1988

[54] CITRIC ACID SALT OF (+) VINPOCETINE

[75] Inventors: Fernando Calvo; Maria T. Manresa, both of Madrid, Spain

[73] Assignee: Covex, S.A., Madrid, Spain

[21] Appl. No.: 6,354

[22] Filed: Jan. 14, 1987

Related U.S. Application Data

[63] Continuation of Ser. No. 706,618, Feb. 28, 1985, abandoned.

[30] Foreign Application Priority Data

Feb. 29, 1984 [ES] Spain ................................ 530.165
Mar. 21, 1984 [ES] Spain ................................ 530.837

[51] Int. Cl.$^4$ .................... A61K 31/44; C07D 461/00
[52] U.S. Cl. ........................................ 514/283; 546/51
[58] Field of Search ............................ 546/51; 514/283

[56] References Cited

U.S. PATENT DOCUMENTS

| | | | |
|---|---|---|---|
| 3,925,393 | 12/1975 | Heurtaux et al. | 546/51 |
| 4,035,370 | 7/1977 | Lörincz et al. | 546/51 |
| 4,065,458 | 12/1977 | Lörincz et al. | 546/51 |
| 4,108,996 | 8/1978 | Lörincz et al. | 546/51 X |
| 4,122,179 | 10/1978 | Vegezzi | 514/283 |
| 4,328,231 | 5/1982 | Zájer née Balázs et al. | 514/283 |

FOREIGN PATENT DOCUMENTS 0154756 9/1985 European Pat. Off. ............ 514/283

OTHER PUBLICATIONS

Lorincz, et al., Chemical Abstracts, vol. 91, 20863r (1979).
Benzi, et al., Chemical Abstracts, vol. 94, 132172h (1981).
Szantay, et al., Chemical Abstracts, vol. 99, 122742h (1983).

*Primary Examiner*—Donald G. Daus
*Assistant Examiner*—Diana G. Rivers
*Attorney, Agent, or Firm*—Fleit, Jacobson, Cohn & Price

[57] ABSTRACT

A (+) citrate salt of vinpocetine, and a procedure for preparing the salt, is disclosed. The salt is useful as a medicinal agent in cerebral-vascular disorders and in neurological treatments relating to cerebral oxygenation, especially in elderly persons.

4 Claims, No Drawings

CITRIC ACID SALT OF (+) VINPOCETINE

This application is a continuation of application Ser. No. 706,618, filed Feb. 28, 1985, now abandoned.

SUMMARY (+) Vinpocetine salts, and the procedures to prepare these salts, especially citrate and phosphate Formulae (I) and (II), which permit rapid absorption, are more soluble in aqueous solutions, increase the pharmacological action of Vinpocetine and present less toxicity than the latter. These salts are useful as medicinal agents in cerebro-vascular disorders and in neurological tratments related to cerebral oxygenation, especially in elderly persons.

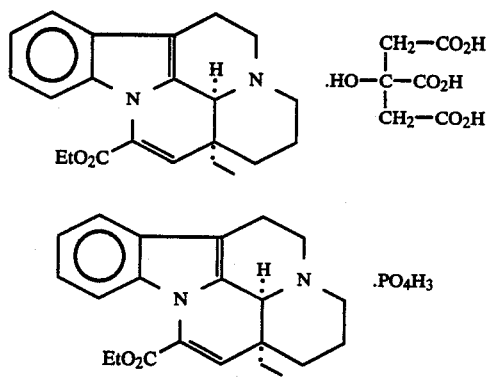

DESCRIPTION

This invention deals with citrate and phosphate Vinpocetine salts, and a specific procedure for obtaining these products.

These compounds respond to general Formulae (I), Citrate, and (II), Phosphate Vinpocetine

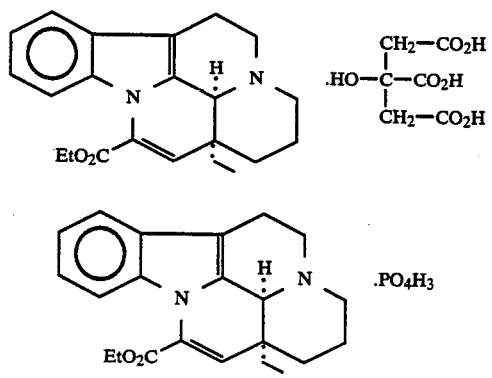

Vinpocetine (3 ox, 16 ox) aburnamenine-14 ethyl carboxilate) is an alkaloid obtained by synthesis from "Vincamina" (Spanish Pat. # 408.180. French Pat. # 2.468.605), which presents a series of very interesting pharmacological properties (Drug. Res. 10, 26, 10, 1976) in relation to cerebral circulation, acting on vascular resistance, especially in the area of cerebral blood vessels.

Under the effects of Vinpocetine blood pressure decreases slightly and cardiac activity also decreases, for which reason it is used for cerebral afflictions accompanied by hypertension. Vinpocetine improves cerebral oxygenation and the anoxic tolerance of the brain cells. Because of its biochemical effects, it increases the concentration of acid AMP, serotomin and ATP in tissues, thus favoring brain function. Similarly, it increases the aerobic and anaerobic metabolism of glucose.

This last issue is what led the applicant to obtain salts from Vinpocetine to improve its action and facilitate absorption. For this purpose a series of salts were prepared based on acids which intervene in the metabolism of glucose. One of the salts that was selected was citrate of (+) Vinpocetine (I) for its pharmacological properties, its rapid absorption by the body and its greater solubility in aqueous solutions which permit the preparation of products that can be used orally, in the form of drops or in injectable solutions.

The pharmacological properties of citrate of Vinpocetine (I) have been used therapeutically with satisfactory results. The relative values are given in the following table:

TABLE

| COMPOUND | $DL_{50}$ | HYPOTENSOR EFFECT | CEREBRUM (BRAIN) | | | |
|---|---|---|---|---|---|---|
| | | | Increased circulation | | Reduction of vascular resistance | |
| | | | i.v. | i.s. | i.v. | i.s. |
| Vinpocetina | 1.0 | 1.0 | 1.0 | 1.0 | 1.0 | 1.0 |
| Citrate of Vinpocetina | 1.5 | 0.8 | 0.8 | 0.7 | 0.9 | 0.6 |

In the study of the effects of this compound, the cerebral circulation (internal carotid artery) has been recorded and calculated, as has vascular resistance. The compounds were administered in intravenous and intra-arterial form, in dogs, and the DL50 values have been determined. The data given in the table above are referred to the data of Vinpocetine to which an arbitrary value of 1.0 has been attributed, i.e., that the relative value obtained by the citrate(I) is high, while its toxicity is low. For the study of the effects on blood pressure and cerebral circulation, intravenous doses of 1 to 4 mg/Kg of animal weight were administered.

The results obtained show that Vinpocetine citrate (I) produces an effective increase in cerebral circulation and presents sufficient diminished toxicity when compared to Vinpocetine base; it being one and a half times less toxic than the latter.

On the other hand, Vinpocetine is insoluble in water which makes it difficult to prepare aqueous dissolutions which can be used orally, in drops or injections, whilst citrate (I) or phosphate (II) of Vinpocetine is soluble in aqueous solutions which permit its oral utilization.

The preparation of citrate (I) is characterized because it is made to react to pure (+) Vinpocetine with a hydroalcoholic or alcoholic solution of citric acid. In this procedure, the alcoholic solution or hydroalcoholic solution of the reaction is subjected to a temperatures of 20 degrees C. for a period of 5 to 10 minutes, with vigorous agitation. When the required time has transpired, half of the volume of the reactions obtained in alcohol media are concentrated, the product is then filtered and can then be used directly in pharmaceutical preparations. The preparation of phosphate (II) is characterized because the (+) Vinpocetine is made to react in an alcohol solution of phosphoric acid. In this procedure, the solution produced by the reaction is subjected to heat, at temperatures ranging between 20 and 70 degrees C., during a period of 3 to 5 minutes, after which time the reaction solutions are cooled to temperatures between 0 and 15 degrees C. producing in this manner the precipitation of the corresponding salt. Likewise, this salt can be prepared from the (+) Vinpocetine salts, such as, for example, hydrochlorate, by making the latter react to sodium or potassium salts of phosphoric acid. Similarly, the citrate (I) can be prepared from other (+) Vinpocetine salts, such as phosphate (II) obtained following the previously described procedure, making it react to sodium or potassium salts of citric acid.

The advantage offered by these procedures is that one can prepare, in a manner that is simple, inexpensive and with satisfactory yields, the citrate (I) and the phosphate (II) of (+) Vinpocetine for therapeutic purposes.

Included herein are some examples of the obtention of citrate (I) and phosphate (II) salts extracted from (+) Vinpocetine by means of this invention.

EXAMPLE 1

2 g. of citric acid are dissolved in 50 ml. of absolute ethanol and to this added 2 g. of (+) Vinpocetine. The mixture is put in reflow for 10 minutes, at the end of which period the solution is concentrated to half of its initial volume and is cooled to 0 degrees C., which precipitates the citrate, which in turn is washed with 2 ml. of absolute alcohol and air-dried, in the absence of light. The product is citrate of (+) Vinpocetine (I) with p.f.: 194–195 degrees C. (Yield: 90%).

EXAMPLE 2

2 g of citric acid are dissolved in 50 ml. of absolute ethanol and 50 ml. of distilled water. To this dissolution 2 g. of (+) Vinpocetine are added and the solution is homogenized to 20 degrees C. temperature and adjusted to a pH 5 to 5.5. The hydroalcoholic solution is brought to a volume of 1000 ml. with distilled water, bringing its pH from 5 to 5.5. The solution is then allowed to rest for 24 hours at the end of which period it is filtered. 2.5 ml. of the prior solution contains 5 mg. of (+) Vinpocetine base, which is the recommended therapeutic dose.

EXAMPLE 3

0.66 g. of sodium citrate are dissolved in 50 ml. of distilled water. Added after this is 1.28 g. of (+) Vinpocetine phosphate (II) and this mixture is agitated at 20 degree C. for 5 minutes and then 50 ml. of absolute ethanol are added. Once these products have solubilized, the solution is filtered by vacuum process and its pH is measured, and adjusted to 5.1. The solution is brought to a volume of 5000 ml. with distilled water. The pH of the solution should be between 5 and 5.1. 2.5 ml. of the solution contains 5 mg. of (+) Vinpocetine base, which is the recommended therapeutic dosage.

EXAMPLE 4

2 g. of phosphoric acid (85%) are dissolved in 50 ml. of ethanol (99%), and added to the previous solution of pure 2 g. of (+) Vinpocetine. The reaction is heated to 60 degrees C. for 5 minutes. Once the reaction is concluded, it is cooled to 0 degrees C., and the precipitated product is filtered and washed with ethanol, dried at 60 degrees C. by vacuum process. 2.3 g. of product are obtained (a 90% yield) with a fusion point of 231–233 degrees C. This solid may be used later in an aqueous solution, in concentrations of 6 to 7 mg/2.5 ml., which is the recommended dosis for pharmaceutical preparations.

EXAMPLE 5

2.65 g. of hydrochloride of (+) Vinpocetine are added to a solution of 1.06 g. of PO4H2Na, in 40 ml. of distilled water and maintaining a termperature of 288 C. The reaction is then subjected to vigorous agitation during a 5 minute period. Once the reaction has concluded, and the steps in Example 4 are followed, obtained is 2.6 g. of phosphate of (+) Vinpocetine (II). Yield: 85%, fusion point 231–233 degrees C.

We claim:

1. A (+) citrate salt of vinpocetine, having the structure set out in Formula (I),

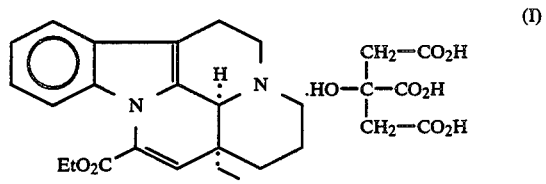

wherein Et represents an ethyl group.

2. A pharmaceutical composition, comprising aqueous and hydroalcoholic dilutions of (+) vinpocetine citrate salt containing about 2 mg of (+) vinpocetine base per milliliter of solution.

3. A pharmaceutical composition according to claim 2 wherein the composition is in the form of oral drops.

4. A pharmaceutical composition according to claim 2 wherein the composition is in injectable form.